US00PP10856P

United States Patent [19]

Covington

[11] Patent Number: Plant 10,856

[45] Date of Patent: Apr. 13, 1999

[54] LANTANA PLANT NAMED 'SONRISE'

[75] Inventor: James Sherrod Covington, Clinton, Miss.

[73] Assignee: Clinton Nursery, Inc., Clinton, Miss.

[21] Appl. No.: 08/929,492

[22] Filed: Sep. 15, 1997

[51] Int. Cl.[6] ..... A01H 5/00

[52] U.S. Cl. ..... Plt./54.1

[58] Field of Search ..... Plt./54.1, 68.1

[56] References Cited

U.S. PATENT DOCUMENTS

P.P. 9,837 3/1997 Roberson ..... Plt./54.1

P.P. 10,156 12/1997 Roberson ..... Plt./54.1

*Primary Examiner*—Howard J. Locker
*Assistant Examiner*—Kent L. Bell
*Attorney, Agent, or Firm*—C. A. Whealy

[57] ABSTRACT

A distinctive cultivar of Lantana plant named 'Sonrise', characterized by its erect and outwardly spreading plant habit; pubescent stems and leaves; floriferousness and lack of seed production; flowers that are golden yellow after opening and become various shades of orange to red, hot pink, and eventually purple during development; and tolerance to low temperatures.

3 Drawing Sheets

The present invention relates to new and distinct cultivar of Lantana plant, botanically known as *Lantana camara*, and hereinafter referred to by the cultivar name 'Sonrise'.

The new cultivar was discovered by the inventor in Clinton, Miss., as a naturally-occurring mutation of the nonpatented *Lantana camara* cultivar 'Ham and Eggs', and was observed in a group of plants of the parent cultivar in July, 1996.

Plants of the new Lantana differ from plants of the parent cultivar 'Ham and Eggs' in flower color. Flowers of the cultivar 'Ham and Eggs' are initially pale yellow after opening and become pale pink during development. However, flowers of the new Lantana are golden yellow after opening and become various shades of orange to red, hot pink, and eventually purple during development.

Asexual reproduction of the new cultivar by cuttings in Clinton, Miss., has shown that the unique features of this new Lantana are stable and reproduced true to type in successive propagations.

The new cultivar has not been observed under all possible environmental conditions. The phenotype may vary significantly with variations in environment such as temperature and light and fertility levels, without, however, any variance in genotype.

The following traits have been repeatedly observed and are determined to be the unique characteristics of plants of the new Lantana and differentiate plants of the new Lantana from other comercial Lantana cultivars:

1. Plants of the new Lantana are erect and outwardly spreading in plant habit.
2. Plants of the new Lantana have very pubescent stems and leaves.
3. Plants of the new Lantana are very floriferous and do not produce seed.
4. Flowers of plants of the new Lantana are golden yellow after opening and become various shades of orange to red, hot pink, and eventually purple during development.
5. Plants of the new Lantana are very tolerant to low temperatures and considered to be hardy to zone 8 of the U.S.D.A. Hardiness Zone Map.

BRIEF DESCRIPTION OF PHOTOGRAPHS

The accompanying colored photographs illustrate the overall appearance and flower color of the new Lantana, showing the colors as true as it is reasonably possible to obtain in colored reproductions of this type.

The photograph on the first sheet of photographs comprises a top perspective view of a typical plant of 'Sonrise' planted in a field situation.

The photograph on the second sheet of photographs comprises a top perspective view of a typical containerized plant of 'Sonrise'.

The photograph on the third sheet of photographs comprises a close-up view of typical flowers of the cultivar 'Sonrise'. Actual flower and foliage colors may differ from flower and foliage colors in the photographs due to light reflectance.

DETAILED BOTANICAL DESCRIPTION

The following observations, measurements and values describe plants grown in Clinton, Miss. and Keller, Tex., under conditions which approximate commercial practice. The plants were initially grown in a polyethylene-covered greenhouse and then moved to a full sun to partial shade field situation during the summer. In the following description, color references are made to The Royal Horticultural Society Colour Chart except where general terms of ordinary dictionary significance are used.

Botanical classification: *Lantana camara* cultivar 'Sonrise'.

Parentage: Naturally-occurring mutation of nonpatented *Lantana camara* cultivar 'Ham and Eggs'.

Propagation:

*Type.*—By cuttings.

*Time to initiate roots.*—10 and 15 days at temperatures of 35 and 21° C, respectively.

*Time to develop roots.*—20 and 25 days at temperatures of 35° and 21° C, respectively.

*Rooting habit.*—Fine, freely branching, and fibrous.

Plant descriptions:

*Plant form.*—Upright and outwardly spreading perennial shrub. Removal of terminal apices enhances branching. Flowers abundant.

*Growth habit.*—Lateral shoots upright, then more outwardly spreading as plants develop. Moderate to vigorous. Time to produce flowers in a one gallon container plants typically about 12 to 16 weeks.

*Plant height.*—About 60 cm.

*Plant width.*—About 60 cm.

*Stem description.*—Lateral branch diameter: About 5 mm. Internode length: About 5 cm. Stem color: 144A. Stem texture: Prickly; very coarse, white and dense hairs.

*Foliage description.*—Leaf arrangement: Opposite. Leaf length: About 7.5 cm. Leaf width: About 5.25 cm. Leaf shape: Ovate. Leaf apex: Acute. Leaf base: Attenuate. Leaf margin: Crenate. Leaf aspect: Mostly flat. Leaf texture: Rough; coarse hairs; upper leaf surfaces more pubescent than lower leaf surfaces. Leaf color: Young foliage, upper surface: Greener than 147A. Young foliage, lower surface: Close to 147B. Mature foliage, upper surface: Close to 147A. Mature foliage, lower surface: Close to 147B. Petiole length: About 1 cm. Petiole diameter: About 2 mm. Petiole color: 144C.

Flower description:

*Flowering habit.*—Scalloped flowers arranged in terminal and axillary heads. Numerous flower heads per plant. Number of flower heads depends on plant size and number of lateral branches developed. Several flower heads per lateral branch in flower simultaneously. Flowers are held upright and are not persistent.

*Natural flowering season.*—Early spring until late fall.

*Quantity of flowers.*—Numerous, usually about 15 flowers per head.

*Flower size.*—Flower heads are about 3.5 cm in diameter; individual flowers are about 1 cm in diameter and about 1 cm in height.

*Peduncle.*—Peduncle angle: About 30° to stem. Strength: Flexible, but hold flowers upright. Color: 144A.

*Flower bud.*—Diameter: About 5 mm. Length: About 5 mm.

*Petals.*—Arrangement: Typically four, occasionally five fused at base. Shape: Rounded, scalloped. Length: About 5 mm. Width: 3 to 5 mm. Tube length: About 1 cm. Tube diameter: About 2 mm. Apex: Rounded. Margin: Entire to slightly fringed. Texture: Smooth. Color: Before opening: Purple, 61A, to orange, 25A/28A. Open flowers: Upper surface: Initially golden yellow, 13A/15A; becoming various shades of orange to red, 28A/33A; becoming hot pink, 54A and purple, 57A; and fading to faint purple, 57C/57D and 55A/55B. Lower surface: Initially yellow, 12A; becoming light orange, 22C/25C; and fading to light pink, 58D/54C.

*Sepals.*—Shape: Lanceolate. Length: About 7.5 mm. Diameter: About 2 mm. Apex: Acute. Margin: Entire. Color: Greener than 147A.

*Reproductive organs.*—Stamens: Quantity: Usually four. Anther shape: Bilobate. Anther length: About 0.5 mm. Pollen color: Golden yellow. Pistils: Length: About 4 mm. Stigma color: Light green. Style color: Light green.

Disease resistance: Resistance to known pathogens of Lantana has not been observed.

*Cold tolerance:* Plants of the new Lantana are very tolerant to low temperatures and considered to be hardy to zone 8 of the U.S.D.A. Hardiness Zone Map.

Seed production: Plants of the new Lantana have not been observed to produce seed and may be sterile.

I claim:

1. A new and distinct Lantana plant named 'Sonrise', as illustrated and described.

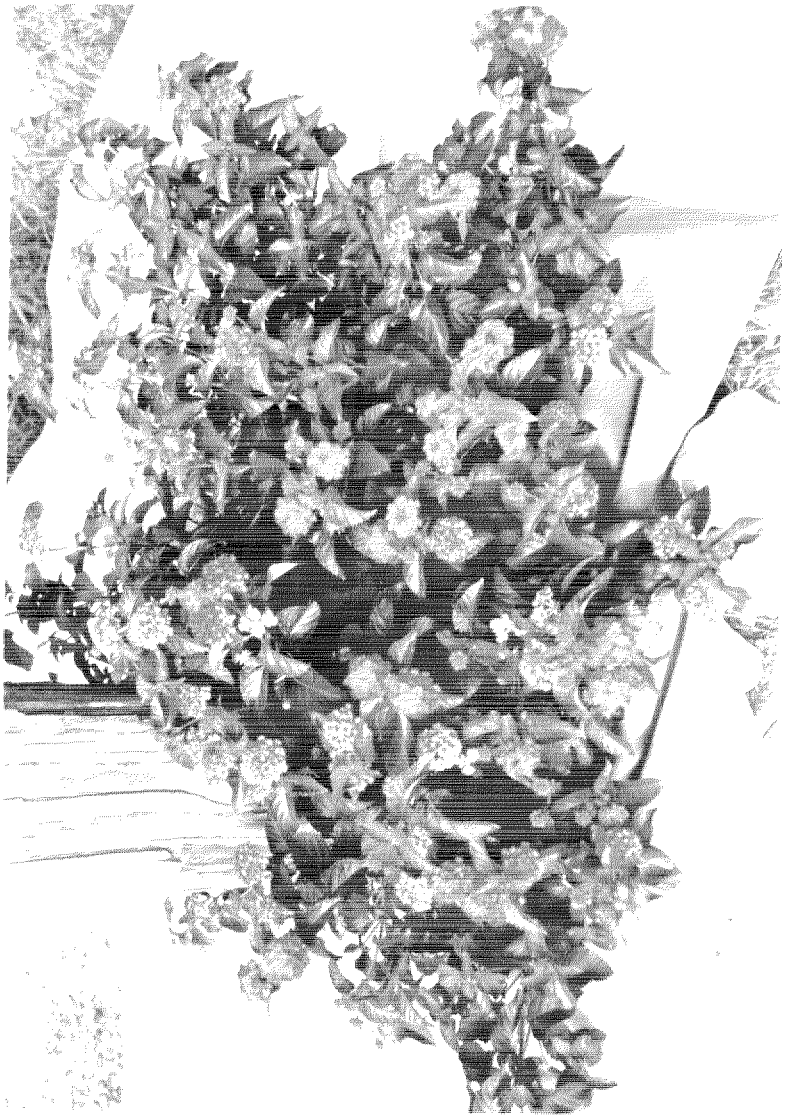

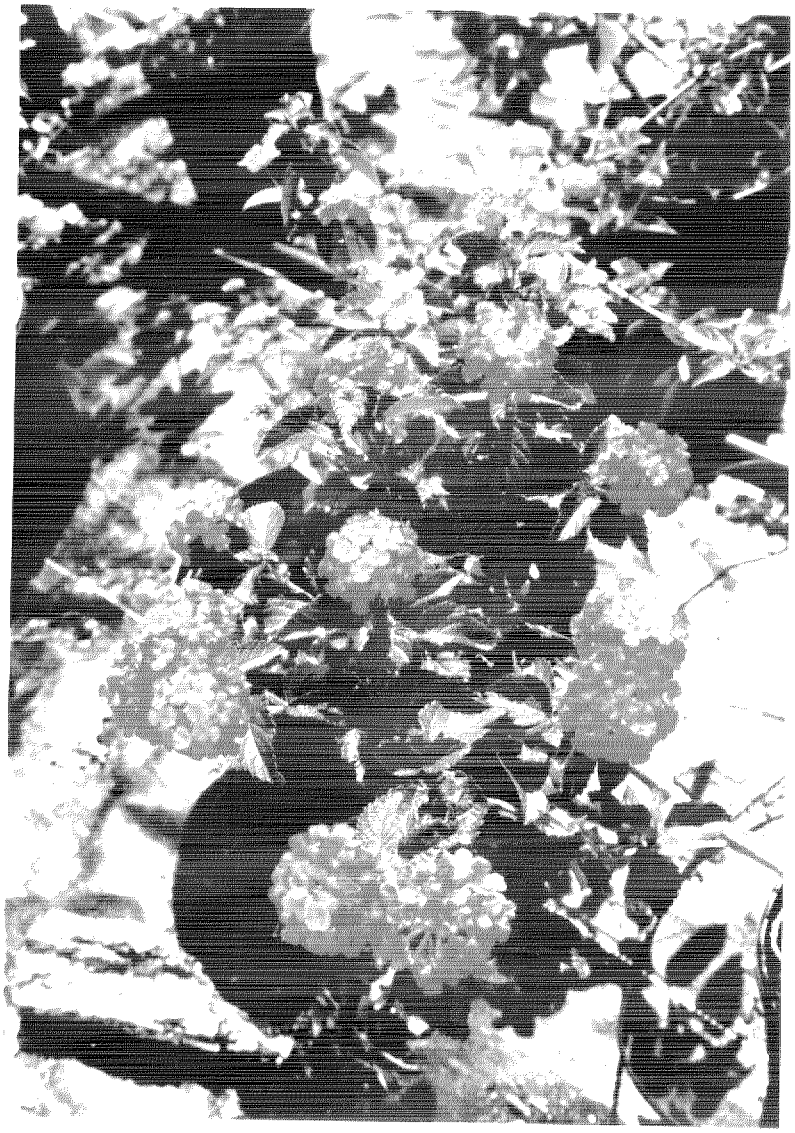

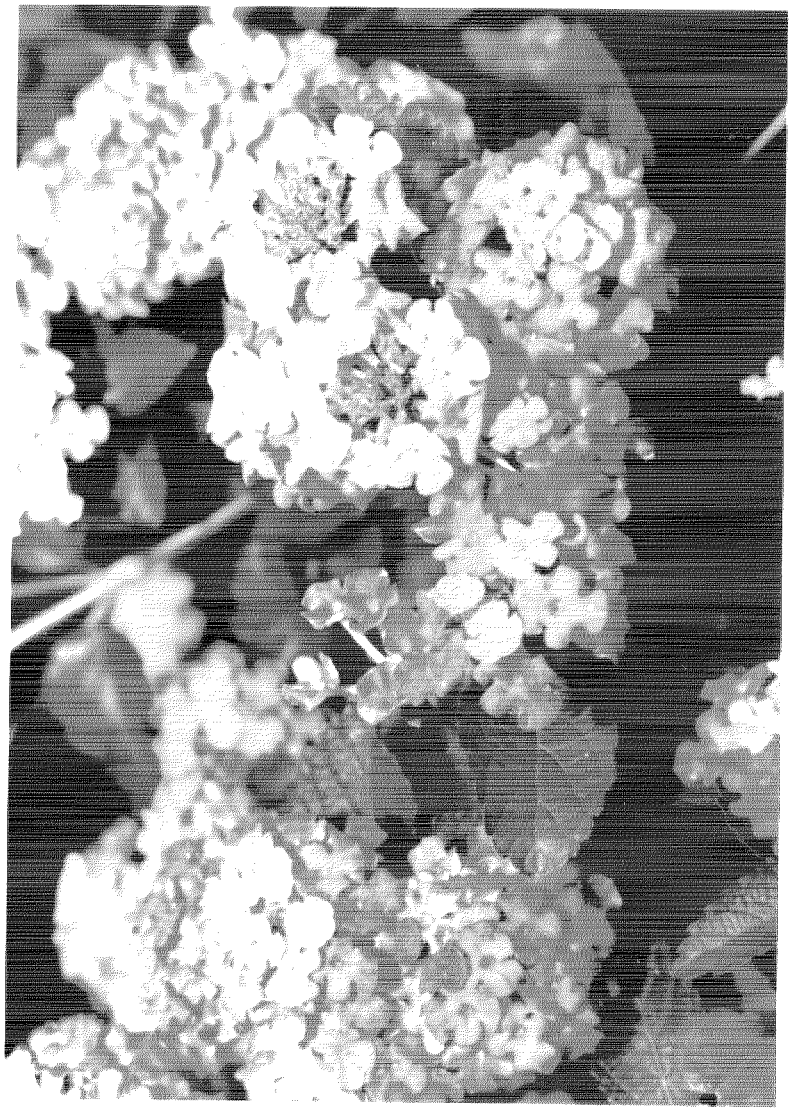

* * * * *